United States Patent [19]

Peacock et al.

[11] Patent Number: 5,001,060
[45] Date of Patent: Mar. 19, 1991

[54] PLANT ANAEROBIC REGULATORY ELEMENT

[75] Inventors: James. W. Peacock, Deakin; John C. Walker, O'Connor; Elizabeth Dennis, Yarramulla, all of Australia; Elizabeth A. Howard, Berkeley, Calif.

[73] Assignees: Lubrizol Enterprises, Inc., Wickliffe, Ohio; Commonwealth Scientific & Industrial Research Organization, Canberra, Australia

[21] Appl. No.: 63,338

[22] Filed: Jun. 15, 1987

Related U.S. Application Data

[63] Continuation-in-part of Ser. No. 11,904, Feb. 6, 1987, abandoned.

[51] Int. Cl.$^5$ .................. C12N 15/00; C07H 15/12
[52] U.S. Cl. ..................... 435/172.3; 435/320.1; 536/27; 935/35; 935/43
[58] Field of Search ............. 435/172.3, 320; 536/27; 935/6, 8, 10, 35, 43

[56] References Cited

PUBLICATIONS

Dennis et al. (1984), Nucleic Acids Res. 12: 3983–4000.
Dennis et al. (1985), Nucleic Acids Res. 13: 727–43.
Llewellyn et al. (1987), J. Mol. Biol. 195:115–123.
Chang C. and Meyerowitz, E. (1986), Proc. Natl. Acad. Sci. U.S.A. 83:1408–1412.
Werr, W. et al. (1985), EMBO J. 4:1373–1380.
Llewellyn et al. (1985), Molecular Form and Function of the Plant Genome, L. Vloten–Doten, G. Groot & T. Hall (eds.) Plenum Press, N.Y., pp. 593–607.
Freeling, M. and Bennett, D. (1985), Ann. Rev. Genet. 19:297–323.
Springer et al. (1986), Mol. Gen. Genet. 205:461–468.
Ellis et al. (1987), EMBO J. 6:11–16.
Ferl (1985), Mol. Gen. Genet. 200:207–210.
Ferl et al. (1987), Plant Mol. Biol 8:299–307.
Paul et al. (1987), Proc. Natl. Acad. Sci. U.S.A. 84:799–803.
Ashraf et al. (1987), Nol. Gen. Genet. 208:185–190.
Ferl and Nick (1987), J. Biol. Chem. 262:7947–7950.
Paul and Ferl (1987) in J. Cell Biochem. Suppl. (11 Part B) Symp. on Plant Gene Systems and Their Biology (Feb. 1987), p. 42.
Vayda and Freeling (1986) Plant Mol. Biol. 6:441–454.

*Primary Examiner*—Charles F. Warren
*Assistant Examiner*—David T. Fox
*Attorney, Agent, or Firm*—Greenlee and Associates

[57] ABSTRACT

DNA sequence elements which effect anaerobic induction of genes in plants are identified and characterized. These sequence elements, designated anaerobic regulatory elements, confer inducibility by anaerobic conditions on downstress plant-expressible promoters and their associated structural genes. In particular, those sequences associated with anaerobic induction of the maize alcohol dehydrogenase and aldolase genes have been identified. These sequence elements can be employed in combination with appropriately positioned plant-expressible genes to produce chimeric, anaerobically inducible genes. Such constructs are useful for the selective expression of structural genes under anaerobic conditions in plants.

21 Claims, 1 Drawing Sheet

```
Maize Adh1

-140        -130            -120              -110       -100
          *           *               *                 *          *
         CTGCAGCCCCGGTTTCG          CAAGCCGCGC         CGTGGTTTGCTTGCC
         -----------------                             --------------
         <    region I   >                             <  region II  >

Maize Adh2

-140         -130              -110       -100
                  *            *                 *          *
         CTGCCTCCCTGGTTTCT  AACCGCGACT(A)10TC   CGAGCCTTTCTTCCC
         ----------------                       ---------------
         <   region I   >                       <  region II  >

Maize Ald1

-70      -60
                           *        *
                      TTTCGCTGGTTTCTTTCCCCTT
```

FIG. I

Maize Adh1

```
    -140       -130                    -120              -110      -100
     *          *                       *                  *        *
CTGCAGCCCCGGTTCG                     CAAGCCGCGC       CGTGGTTTGCTTGCC
_____                                      _____
  < region I  >                                         < region II >
```

Maize Adh2

```
            -140          -130                    -110      -100
             *             *                        *        *
        CTGCCTCCCTGGTTCT AACCGGACT(A)₁₀TC      CGAGCCTTTCTTTCCC
        _____                           _____
          < region I  >                              < region II >
```

Maize Ald1

```
          -70          -60
           *            *
    TTTCGCTGGTTTCTTTCCCCTT
         _____
```

PLANT ANAEROBIC REGULATORY ELEMENT

This application is a continuation-in-part of co-pending application Ser. No. 011,904, filed Feb. 6, 1987, now abandoned.

FIELD OF THE INVENTION

This invention relates to the field of plant molecular biology in general, and in particular to sequences which regulate gene expression in response to anaerobic conditions. This invention will enable the selective expression of desired structural genes under anaerobic conditions in either monocotyledonous or dicotyledonous plants.

BACKGROUND OF THE INVENTION

Higher plants are obligately aerobic organisms, that is, they require oxygen for survival and growth. Natural environmental conditions would never expose a plant to total anaerobiosis, but temporary flooding or waterlogging of soil can lead to anoxia in the root zone. Plants have evolved adaptive responses to survive the stress of transient anaerobic conditions. Some plants, such as rice, are tolerant of prolonged flooded conditions due to specialized tissue which transfers oxygen from the upper portions of the plant to the submerged root tissue; this specialized tissue is known as the aerenchyma. Maize is an example of a species which tolerates relatively short-term flooding. A specific set of proteins is induced in plants during anaerobic conditions which affect changes in the energy metabolism of the root cells to fit the altered environmental conditions.

The plant anaerobic response has been well studied over the last several years. M. Sachs et al. (1980), Cell 20:761-767, described the patterns of anaerobic protein synthesis in maize seedling roots; relatively few proteins were synthesized, and similar patterns were observed in rice, sorghum, tragopogon, barley, peas, and carrots. R. Okimoto et al. (1980), Planta 150:89-94, extended these observations and demonstrated that although the patterns of aerobic protein synthesis in the various plant tissues were very different, the profiles of proteins synthesized in those tissues under anaerobic conditions were very similar. In maize there are about ten major and ten minor anaerobic proteins (ANPs). Because the ANPs synthesized in a variety of plants are similar and because synthesis displays little tissue specificity, it appears that these proteins are the products of a set of genes whose expression is induced in response to adverse environmental conditions, and that the ANPs may be analogous to the heat shock proteins induced by thermal stress.

The importance of alcohol dehydrogenase in the survival of maize during temporary anaerobiosis has long been known. D. Schwartz (1969), Amer. Nat. 103:479-481, demonstrated that ADH+ and ADH− seeds germinated equally well unless the seeds had been exposed to anaerobic conditions. It was later shown that there were two genes encoding alcohol dehydrogenase in maize, Adh1 and Adh2. Both Adh1 and Adh2 are induced after the onset of anaerobiosis (M. Freeling (1973), Mol. Gen. Genet. 127:215-227). Of the two enzymes, Adh1 is the one of primary importance during anaerobic conditions (M. Freeling and D. Schwartz (1973), Biochem. Genet. 8:27-36). During anaerobiosis, oxygen is no longer available to serve as the terminal electron acceptor. Cells adapt to this by increasing glycolysis and turning to ethanolic fermentation, rather than allowing lactic acid to accumulate in the tissue. J. Roberts et al. (1984), Proc. Nat. Acad. Sci. USA 81:3379-3383, and 6029-6033, have shown that ADH− cells undergo a severe drop in intracellular pH due to leakage of protons from the vacuole; in ADH+ cells there is only a slight drop in the intracellular pH. It is believed that the severe decline in intracellular pH is what causes death in the ADH− cells.

The functions of several of the other ANPs of maize have been described. Sucrose synthase, formerly known as ANP87 (87 kd protein) has recently been identified by Freeling and Bennett (1985) Ann. Rev. Genet. 19:297-323. Sucrose synthase is encoded by the Sh1 gene of maize, which has recently been cloned and sequenced (Werr et al. (1985), EMBO J. 4:1373-1380). In anaerobic roots, sucrose synthase catalyzes the hydrolysis of sucrose to fructose and glucose to supply hexose to the cells for glycolysis and energy generation. Two other ANP enzymes which participate in glycolysis are phosphohexose isomerase (P. Kelley and M. Freeling (1984), J. Biol. Chem. 259:673-677) and fructose 1,6-diphosphate aldolase (K. Wignarajah and H. Greenway, (1976), New Phytol. 77:575-584; P. Kelley and M. Freeling (1984), J. Biol.Chem. 259:14180-14183). A sixth identified ANP is pyruvate decarboxylase (K. Wignarajah and H. Greenway, supra; A. Laszlo and P. St. Lawrence (1983), Mol. Gen. Genet. 192:110-117).

Maize Adh1 has been cloned and sequenced (E. Dennis et al. (1984), Nucleic Acids Res. 12:3983-4000) as has been Adh2 (E. Dennis et al. (1985), Nucleic Acids Res. 13:727-743). Pea Adh1 has recently been cloned and sequenced as well D. Llewellyn et al. (1987) J. Mol. Biol. 195:115-123). The availability of sequence information for the pea gene and several of the maize genes and the growing body of knowledge that nucleotide sequences in the 5' untranscribed regions of both eukaryotic and prokaryotic genes regulate gene expression have led to a search for the sequence information which directs anaerobic induction. Therefore, sequences upstream of several of these genes have been compared with the goal of finding the anaerobic regulatory element(s).

Sequences governing eukaryotic gene expression are the subject of intensive study. Promoter sequence elements include the TATA box consensus sequence (TATAAT), which is typically positioned 20 to 30 bp upstream of the transcription start site. By convention, the start (or cap) site is called +1, and sequences extending in the 5' (upstream) direction are given negative numbers; thus the TATA box would be in the vicinity of −20 to −30. In most instances the TATA box is required for accurate −80 and −100, there can be a promoter element with transcription initiation. Further upstream, often between homology to the consensus sequence CCAAT (R. Breathnach and P. Chambon (1981), Ann. Rev. Biochem. 50:349-383). In plants there can be instead an AGGA element, in which there is a symmetry of adenines surrounding the trinucleotide G(orT)NG (J. Messing et al. (1983), in *Genetic Engineering in Plants*, eds. T. Kosuge, C. Meredith, and A. Hollaender, pp 211-227).

In animal and yeast systems there is a relatively large body of knowledge describing sequences not necessarily within the promoter which modulate gene expression. One such sequence element is the enhancer, which is defined by G. Khoury and P. Gruss (1983), Cell 33:313-314, as a sequence which increases transcriptional efficiency in a manner relatively independent of position and orientation with respect to a nearby gene. The prototype enhancer is the 72 bp tandem repeat of SV40, which contains the core consensus sequence GGTGTGGAAA(or TTT)G. Generally enhancers in animal systems can act from a position either 5' or 3' to the gene, and can act over distances of one or more kb. In yeast there are sequences located 5' to the transcriptional start site known as upstream activating sequences (UAS's), which may also carry regulatory information. Like the animal enhancers, the yeast UAS's can function in either orientation; however they do not appear to stimulate transcription when placed 3' to the transcription start site (B. Errede et al. (1985), Proc. Nat. Acad. Sci. USA 82:5423–5427; L. Guarente and E. Hoar (1984), ibid. 81:7860–7864; G. Roeder et al. (1985), ibid. 82:5428–5432; K. Struhl (1984) ibid. 7865–7869).

Recently some data have appeared regarding enhancer-like sequences in plant and plant virus genes. J. sequences between −105 and −46 are required for maximal expression of the Cauliflower Mosaic Virus (CaMV) 35S promoter. Contained within that region is a sequence partially homologous to the animal enhancer core consensus sequence, but its functionality has not yet been established. There are other examples of sequences in plant DNA with homology to the animal core consensus sequence, including one in the 5' untranscribed region of the pea legumin gene (G. Lycett et al. (1984), Nucleic Acids Res. 12:4493–4506) and another upstream of the Antirrhimun majus chalcone synthase gene (H. Kaulen et al. (1986), EMBO J. 5:1–8), and several similar sequence motifs located 5' to light-regulated ribulose bis-phosphate carboxylase small subunit genes in Petunia, pea, and tobacco (reviewed by R. Fluhr et al. (1986), Science 232:1106–1112). In none of these cases has it been demonstrated that these plant sequences with homology to the animal enhancer core consensus sequence have activity.

Definitive experiments regarding a plant-active transcription activating element have been performed by J. Ellis et al. (U.S. patent application Ser. No. 011,614, filed Feb. 6, 1987 now pending). A sequence partially homologous to the SV40 core consensus sequence was found in the 5' region of the *Agrobacterium tumefaciens* T-DNA gene encoding octopine synthase (ocs), which is expressed in infected plant cells and tissues. Deletion of this SV40-like sequence was however shown to have no effect on the level of expression of a downstream gene. It was established, however, that a 16 bp palindromic sequence (5'-ACGTAAGCGCTTACGT-3') not part of the SV40 homologous region was necessary as a part of the ocs-derived fragment or sufficient when inserted as a chemically synthesized oligonucleotide to give transcriptional activation.

There are other sequences known to be present in the 5' flanking regions of genes which regulate the expression of those genes in response to environmental signals. Thermal stress elicits the expression of a family of genes called the heat shock proteins (HSPs); gene induction by elevated temperature requires the presence of a characteristic sequence motif, or heat shock element (HSE). The consensus sequence for the HSE is 5'-CTGAAT-TTCTAGA-3' (H. Pelham and M. Bienz (1982), in *Heat Shock: From Bacteria to Man,* eds. M. Schlessinger, M. Ashburner, and A. Tissieres, Cold Spring Harbor Laboratory, pp. 43–48). These sequences interact with a heat shock specific transcription factor which allows the induction of the HSP genes (C. Parker and J. Topol (1984), Cell 37:273–283). It is likely that a similar mechanism functions in higher plants because sequences with significant homology to the above HSE have been located in the 5' flanking regions of several soybean heat shock genes (F. Schoffl et al. (1984), EMBO J. 3:2491–2497; E. Czarnecka et al. (1985), Proc. Nat. Acad. Sci. USA (1985) 82:3726–3730; Key et al., U.S. patent application Ser. No. 599,993, filed Apr. 13, 1984). In maize the hsp70 gene has been cloned and sequenced, and carries two copies of the HSE 5' to the transcription start site (D. Rochester et al. (1986), EMBO J. 5:451–458).

Metallothioneins are another class of proteins whose synthesis is induced by stress: in this case by exposure to (toxic) heavy metals in the environment. These genes have in their 5' untranscribed regions copies of a DNA sequence motif called the metal regulatory element (MRE) (reviewed by D. Hamer (1986), Ann. Rev. Biochem. 55:913–951). The mammalian consensus sequence is 5'-TGCGCYCGGCCC-3'. These genes have been well studied in mammalian and yeast systems, but there is no sequence data for cabbage, tomato, and tobacco.

In plants there is a growing interest in the cis-acting sequences which mediate light-regulation and tissue specificity. M. Timko et al. (1985), Nature 318:579–582, described experiments in which the −973 to −90 region of 5' flanking DNA was active, in either orientation, in stimulating expression from the pea ribulose bis-phosphate carboxylase small subunit rbcS ss3.6 gene promoter after illumination. J. Simpson et al. (1985), EMBO J. 4:2723–2729, presented evidence that the 400 bp preceding the pea chlorophyll a/b binding AB80 protein gene carried the sequence information necessary for light regulation and tissue specificity. R. Fluhr et al. (1986), Science 232:1106–1112, showed that the −327 to −46 region 5' to the rbcS-3A gene of pea conferred tissue specificity and light response on a heterologous promoter. The −317 to −82 region of the rbcS-E9 gene gave similar results. The exact sequences directing these responses have not yet been defined.

The existence of known sets of anaerobically induced proteins in several different plant species has led to the hypothesis that there may be a cis-active sequence or sequences which occurs 5' to the structural genes within the ANP group. The availability of sequence information for the maize Adh1 (E. Dennis et al. (1984), Nucleic Acids Res. 12:3983–4000), maize Adh2 (E. Dennis et al. (1985), Nucleic Acids Res. 13:727–743), maize Sh1 (W. Werr et al. (1985), EMBO J. 4:1373–1380), pea Adh1 (D. Llewellyn et al. (1986), manuscript submitted), and *Arabidopsis Adh* (C. Chang and E. Meyerowitz (1986), Proc. Nat. Acad. Sci USA 33:1408–1412), has prompted a comparison of 5' flanking regions with the goal of identifying conserved sequences which might play a regulatory role in the anaerobic induction of those genes.

In D. Llewellyn et al. (1985), in *Molecular Form and Function of the Plant Genome,* eds. L. Vloten-Doten, G. Groot, and T. Hall, New York: Plenum Press, pp. 593–607, and in E. Dennis et al. (1985), Nucleic Acids Res. 13:727–743, one sequence proposed to be involved in anaerobic regulation of maize Adh1 and Adh2 is 5'-CACCTCC-3'. Interestingly, this sequence is 80% homologous to the complement of the animal enhancer core consensus sequence. M. Freeling and D. Bennett (1985), Ann. Rev. Genet. 19:297–323, speculated that the sequence 5'-TGGGG-3', present in multiple copies upstream of the two maize Adh genes, might be a potential regulatory sequence. They also noted that this sequence was found in association with a sequence similar to the animal enhancer core consensus sequence.

In Llewellyn et al. (1985), supra, there were also two other sequences, with partial homologies 5' to the maize Adh1 and Adh2 genes. In that publication they stated that there was no experimental evidence that these sequences functioned to regulate gene expression. In the present work provides the first documentation that portions of these sequences function in the anaerobic response. The present work identifies sequences in maize Adh1, Adh2 and aldolase gene 5' untranslated regions that confer anaerobic regulation on heterologous genes placed under their control. These anaerobic regulatory sequences function for anaerobic gene expression in plant species other than maize. The DNA sequences, DNA fragments containing them and constructions of the present invention will enable others to selectively express structural genes under anaerobic conditions in plant tissue.

SUMMARY OF THE INVENTION

A primary object of this invention is to provide a method which will enable those skilled in the art to selectively express structural genes in plants under anaerobic conditions. This object is to be accomplished by utilizing DNA sequences, which we have termed the anaerobic regulatory element, from the 5' untranscribed regions of anaerobically regulated plant genes which confer anaerobic inducibility on genes placed under their control. In the preferred embodiment, those sequences are derived from the upstream region of the maize alcohol dehydrogenase 1 gene and the maize aldolase gene.

It has been found in the maize Adh1 gene that the anaerobic regulatory element comprises two sequence regions important for anaerobic induction, region I and region II. In the preferred embodiment, the Adh1 gene sequences, region I is positioned in the 5' untranslated region of the gene between about nucleotide $-140$ to $-124$. The $-140/-124$ sequence of Adh1 is

5'-CTGGAGCCCCGGTTTCG-3'

Region II in the Adh1 gene is positioned between about nucleotide $-113$ and $-99$. The $-113/-99$ sequence of Adh1 is

5'-CGTGGTTTGCTTGCC-3'.

Maize Adh2 gene upstream sequences homologous to the sequences which delimit the Adh1 anaerobic regulatory element components have also been identified. A region 76% homologous (13 out of 17 sequence matches) to the $-140/-124$ Adh1 sequence was found between nucleotide $-150/-134$. The $-150/-134$ sequence of Adh2 is

5'-CTGCCTCCCTGGTTTCT-3'.

A region 66% homologous (10 out of 15 matches) to the $-113/-99$ Adh1 sequence was found between nucleotide $-110$ to $-96$. The $-111/-97$ sequence of Adh2 is

5'-CGAGCCTTTCTTCCC-3'.

The 5' untranslated region of the maize aldolase gene was found to contain a single sequence element which is homologous to portions of the Adh1 and Adh2 sequences associated with both regions I and II. This 10 bp sequence extending from about position $-59$ to $-68$ has the sequence:

5'-GCTGGTTTCT-3'.

This element functions in the anaerobic regulation of the maize aldolase gene and constitutes the anaerobic regulatory element of aldolase.

Functional plant anaerobic regulatory elements can be derived from anaerobically induced genes from alternate sources, which include, but are not limited to, those of monocots, such as sequences from the upstream regions of the genes for maize alcohol dehydrogenase (Adh2 and Adh1) and maize aldolase.

The method of this invention involves the construction of a recombinant DNA molecule which comprises an anaerobic regulatory element, a plant-expressible promoter and a plant-expressible structural gene, the plant-expressible structural gene being located 3' to the plant-expressible promoter and positioned such that expression of the structural gene is controlled by the promoter, the promoter/structural gene combination being positioned 3' to the anaerobic regulatory element, so that the anaerobic regulatory element affects anaerobic induction of the structural gene. The anaerobic regulatory element should be placed between about 10 and about 500 bp 5' to downstream signals for transcription initiation, and preferably located between about $-60$ and about $-160$ bp 5' to the transcription start site, as measured from the 3' end of region II. The construction of such a DNA molecule is accomplished by conventional techniques using plant anaerobic regulatory elements as described above. Further the construction of such a DNA molecule can employ specific maize DNA fragments described herein which have been shown to confer anaerobic induction on heterologous genes placed downstream from them and under their regulatory control. These maize DNA fragments may contain other functional sequences in addition to anaerobic regulatory elements including enhancer function(s) and or a promoter. It is contemplated that any plant expressible promoter can be employed in these constructions. It is preferred that the promoter of an anaerobically induced plant gene be employed. Such promoters include but are not limited to the promoters of plant alcohol dehydrogenase and sucrose synthase genes particularly those of the maize Adh1, maize Adh2, pea Adh1 and the maize sucrose synthase genes. It is most preferred that the promoter of maize Adh1 be employed in such constructions. It is contemplated that any plant-expressible structural gene can be employed in these constructions.

After construction, the DNA molecules described above are introduced into plant tissue, so that the anaerobic regulatory element/promoter/structural gene combination is expressed under anaerobic conditions in that tissue. Transformation of plant cells and tissue with exogenous or foreign DNA can be achieved in a number of ways known to the art. In the preferred embodiment, the technique of electroporation was used.

After introduction of the anaerobic regulatory element/promoter/structural gene combination into plant tissue, expression of the structural gene is induced by application of anaerobiosis on the transformed plant tissue or cells. Since plant cells and tissue will not survive under completely anaerobic conditions, some oxygen must be supplied. It has been found that $O_2$ provided at a level of about 5% v/v of the total atmosphere, induces anaerobic condition in plant cells and induces a full anaerobic induction response, but allows cell survival. Partial anaerobic induction can be obtained by subjecting plant tissue to atmospheres containing less than 20% oxygen (normal atmospheric conditions), for example atmospheres containing about 10% oxygen. Oxygen levels of about 1% induce measurable anaerobic induction; however, plant cells rapidly die. Anaerobiosis is preferably induced by placing transformed plant tissue in an atmosphere comprising 5% $O_2$/95% $N_2$ (v/v).

The method of the present invention is generally applicable to the anaerobic expression of structural genes in both monocotyledonous and dicotyledonous plants. The method is particularly applicable to maize and tobacco plant tissues. Another object of this invention is to provide recombinant DNA molecules which comprise an anaerobic regulatory element as detailed above, plant-expressible promoter sequences located 3' to the anaerobic regulatory element, and a plant-expressible structural gene located 3' to said plant-expressible promoter such that the structural gene is placed under the regulatory control of the promoter and anaerobic regulatory element. Other objects of this invention are plants, plant cells and plant tissue containing the DNA molecules described herein and prepared by the methods described herein.

BRIEF DESCRIPTION OF THE FIGURE

FIG. 1 is a comparison of conserved DNA sequences within the anaerobic regulatory elements from several anaerobically induced genes of maize. Adh1 and Adh2 sequences are aligned for comparison. The sequences are numbered from the transcription start (CAP site). Adh1 is as published in Dennis et al., 1984, except at original positions −123 to −121 which on resequencing in the present work was found to contain CC rather than CAC. The sequence has been renumbered according to a correction (Ellis et al., 1986, submitted). Adh1I numbering is as reported in Dennis et al. (1985) and Llewellyn et al. (1985). The sequence regions that delimit regions I and regions II of the ARE of Adh1 and Adh2 are underlined (solid line). The portions of the Adh1 and Adh2 ARE's that show homology to the maize Adh1 ARE are also underlined (broken line).

DETAILED DESCRIPTION OF THE INVENTION

The following definitions are provided in order to remove ambiguities in the intent or scope of their usage in the specification and claims.

Expression refers to the transcription and translation of a structural gene so that a protein is synthesized.

Chemically synthesized, as it relates to a sequence of DNA, means that the component nucleotides were assembled in vitro by nonenzymatic means. Chemical synthesis may be automated, as performed by commercially available equipment, or manual synthesis may be accomplished by techniques known to those skilled in the art (e.g. Caruthers (1983) in *Methods of DNA and RNA Sequencing*, Weissman (ed.) Praeger Publishers (New York), Chapter 1).

A promoter refers to the sequences at the 5' end of a structural gene which direct the initiation of transcription. Promoter sequences are necessary, but not always sufficient, to drive the expression of a downstream gene. Eukaryotic promoters generally contain a sequence with homology to the consensus 5'-TATAAT-3' (TATA box) about 10–35 bp 5' to the transcription start (cap) site, which is by convention numbered +1; bases 3' to the cap site are given positive numbers while bases 5' to the cap site receive negative numbers reflecting their distances from the cap site. About 30–70 bp 5' to the TATA box there is often another promoter component with homology to the canonical form 5'-CCAAT-3' (R. Breathnach and P. Chambon (1981), Ann. Rev. Biochem. 50:349–383). In plants the CCAAT "box" is sometimes replaced by the AGGA "box", a region with adenine residues symmetrically flanking the triplet G(or T)NG (J. Messing et al. (1983), in *Genetic Engineering of Plants*, eds. T. Kosuge, C. Meredith, and A. Hollaender, Plenum Press, pp. 211–227). Other sequences conferring tissue specificity, response to environmental signals, or maximum efficiency of transcription may be found interspersed with these promoter elements or found further in the 5' direction from the cap site. Such sequences are often found within 400 bp of the cap site, but may extend as far as 1000 bp or more.

The term anaerobic regulatory element described herein refers to DNA sequences which confer inducibility by hypoxic conditions on downstream promoters and the associated structural genes. Anaerobic induction or inducibility means that gene expression increases during anaerobic conditions. In some cases, a gene will be expressed only under anaerobic conditions; in other cases, the imposition of anaerobiosis causes a marked increase in expression of a gene that is expressed under aerobic conditions. The expression of plant Adh genes is not detected under aerobic conditions. In contrast, plant aldolase genes are expressed at a low level under aerobic conditions but their expression is increased under anaerobic conditions.

There is also tissue specificity expression of certain anaerobically regulated genes. In immature endosperm Adh1, Adh2 and sucrose synthase are expressed in the absence of external anaerobic conditions. This tissue specific expression could, however, result from low oxygen tension with the endosperm tissue. There appear to be several cases in which tissue specific expression apparently overrides anaerobic regulation. There is expression of the maize Adh1 gene in pollen which appears not to be due to anaerobic induction since other ANPs, like Adh2, are not expressed (Freeling (1976) Genetics 83:701–717). Conversely, there are apparently regulatory functions, also possibly tissue specific or linked to development, which act to suppress the anaerobic response. For instance, mature leaves do not show expression of ANPs even after prolonged anaerobic induction (Okimoto et al. (1980) Planta 150:89).

In the 5' untranscribed portion of the maize Adh1 gene, the region between −140 and −99 has been found to be essential for anaerobic regulation of Adh-/cat chimaeric genes. Sequences upstream of position −140 enhance the expression of such genes. The anaerobic regulatory element (ARE) of the Adh1 gene comprises sequences within this −140/−99 region. The ARE of Adh1 is composed of two essential sequence components. Region I is delimited by nucleotide positions −140 to −124, having the sequence 5'-CTGCAGCCCCGGTTTCG-3'; region II is delimited by nucleotide positions −113 to −99, having the sequence 5'-CGTGGTTTGCTTGGGCC-3'. Mutation of region I resulted in a low constitutive level of expression, while mutation of region II resulted in no observable expression above background. Mutations of the sequences between these two regions do not significantly alter anaerobic expression, indicating that the intervening sequences do not contain sequences important for anaerobic regulation. Each of these regions was used independently to search for anaerobic regulatory element homologous regions in the 5' untranscribed regions of three other plant anaerobically induced genes with known DNA sequence: maize Adh2 (Dennis et al. 1985), pea Adh1 (Llewellyn et al. 1986) and maize Sh1 (Werr et al. 1985). Homologous regions in these genes were identified using the criteria of DNA sequence homology and position. The position requirements were that Region I be 5' to Region II, that Region II be 5' to the TATA and CAAT box promoter elements of the genes, and that Region I be within 300 bp of the transcription start site.

There is substantial sequence conservation between the ARE regions of Adh1 and portions of the 5' untranslated region of the maize Adh2 gene. An Adh2 sequence 76% homologous to the $-140/-124$ region I sequence is positioned between nucleotides $-150$ and $-134$ and has the sequence 5'-CTGCCTCCCTGGTTTCT-3'. An Adh2 sequence 66% homologous to the $-113/-99$ region II sequence is positioned between nucleotides $-111$ and $-97$ and has the sequence 5'-CGAGCCTTTCTTCCC-3'. The region I and region II sequences of Adh1 and Adh2 are compared in FIG. 1.

Homologies of regions I and II of maize Adh1 to pea Adh1 and maize Sh1 were less striking. Two sequences in the maize Sh1 5' untranslated region extending from $-242$ to $-226$ and from $-219$ to $-204$ are 55% (10 out of 17) and 53% (8 out of 15) conserved with region I and region II of Adh1, respectively. In the pea Adh1 5' untranslated region no sequences having greater than about 50% homology with the Adh1 region I and region II was identified.

An 877 bp portion of the 5' untranslated region of the maize aldolase gene extending from nucleotide $-805$ to $+72$ was found to confer anaerobic inducibility on a chimaeric Aldolase/cat gene. The sequence of the 5' untranslated region of aldolase was examined for homology to the ARE regions of maize Adh1. A 10 bp Aldolase sequence 5'-GCTGGTTTCT-3' having homology to portions of both region I and region II was identified. No other significant sequence homologies to regions I and II were found. The 10 bp Aldolase sequence is located about 40 bp upstream of the TATA box at position $-59$. The aldolase sequence and region II of Adh1 both contain the hexanucleotide TGGTTT. The Adh1 region I sequence contains a partial iteration of the same motif GGTTT. The maize Adh2 ARE sequences contain the sequence TGGTTTCT, however the exact iteration is located in the region I sequence of Adh2. Region II of Adh2 also contains some homology to the 10 bp aldolase sequence at sequence TTTCT.

Springer et al. (1986) Mol. Gen. Genet. 205:461 identified a 13 bp sequence (5'-CGTGGTTTGCTTG-3') in the first intron of maize sucrose synthase gene which is homologous to the Adh1 region II. No functional analysis of this region in the sucrose synthase intron was reported. Springer et al. (1986) do report that no extended homology to Adh1 was found in the sucrose synthase upstream regions. In contrast, the inventors have identified a region of homology to the aldolase 10 bp sequence in the sucrose synthase upstream region, between nucleotide positions $-162$ to $-170$, which has the sequence 5'-CTGGTTTTG-3'. From a comparison of the aldolase sequence and those Adh1 and Adh2 sequences homologous to it, a consensus sequence 5'-BBTGGTTTBB-3' emerges, where B=C or G or T. This consensus sequence appears to function in anaerobic regulation and may represent a binding site of a common protein trans acting factor. Regions I and II of the AREs of Adh1 and Adh2 may represent double iterations of the potential binding motif.

It is interesting to note that no significant conservation of the ARE sequences of maize Adh1 and Adh2 or aldolase is found in the upstream regions of pea Adh1. The complement of part of the 10 bp aldolase element (AAACCA) is located in the pea Adh1 upstream region at about $-100$. A similar complement of the aldolase region is found in the upstream region of the *Arabidopis thaliana* gene at about position $-155$.

Regulatory control refers in general to the modulation of gene expression induced by DNA sequence elements, particularly those located upstream of (5' to) the transcription start site. Regulation may be analogous to an on/off switch which responds to environmental conditions, or regulation may result in variations in the level of gene expression. Herein, the anaerobic regulatory element functions in such a way that downstream gene expression results only when environmental conditions are anaerobic. Partial anaerobic induction occurs under partial anaerobic conditions.

Placing a structural gene under the regulatory control of a promoter or a regulatory sequence element means positioning the structural gene such that the expression of the gene is controlled by these sequences. Promoters are generally positioned 5' (upstream) to the genes that they control, as described above. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art and demonstrated by the anaerobic regulatory elements described herein, some variation in this distance can occur.

A structural gene is that portion of a gene comprising a DNA segment encoding a protein, polypeptide, or a portion thereof. The term can refer to copies of a structural gene naturally found within the cell, but artificially introduced, or the structural gene may encode a protein not normally found in the plant cell into which the gene is introduced, in which case it is termed a heterologous gene. A heterologous structural gene may be derived in whole or part from a bacterial genome or episome, eukaryotic genomic or plastid DNA, cDNA, viral DNA, or chemically synthesized DNA. It is possible that a structural gene may contain one or more modifications in either the coding or the untranslated regions which could affect the biological activity or the chemical structure of the expression product, the rate of expression, or the manner of expression control. Such modifications include, but are not limited to, mutations, insertions, deletions, and substitutions of one or more nucleotides. The structural gene may constitute an uninterrupted coding sequence or it may include one or more introns, bounded by the appropriate plant-functional splice junctions. The structural gene may be a composite of segments derived from a plurality of sources, naturally occurring or synthetic. The structural gene may also encode a fusion protein, so long as the experimental manipulations maintain functionality in the joining of the coding sequences.

Plant tissue includes differentiated and undifferentiated tissues of plants, including, but not limited to, roots, shoots, leaves, pollen, seeds, tumor tissue, and various forms of cells in culture, such as single cells, protoplasts, embryos and callus tissue. The plant tissue may be in planta or in organ, tissue, or cell culture.

Anaerobic conditions refer to the flooding of seedlings or mature plants so that root tissue becomes hypoxic. In the case where the experimental plant tissue comprises cultured cells or protoplasts, an atmosphere containing about 5% oxygen/95% nitrogen atmosphere constitutes functionally anaerobic conditions. Protoplasts, plant cells and plant tissue die under strict anaerobic conditions. Oxygen levels above between about 5% (normal atmospheric oxygen concentration) are partial anaerobic conditions. Plant tissue placed under partial anaerobiosis will display an attenuated anaerobic response. Plant tissue placed under about 1% oxygen concentrations will display anaerobic induction; however, plant cells rapidly die. It is contemplated that other inert, non-toxic gases, for example argon, in place of or in combination with nitrogen.

Production of genetically modified plant tissue expressing a structural gene under the control of an anaerobic regulatory element and a downstream promoter combines the teachings of the present disclosure with a variety of techniques and expedients known in the art. In most instances alternative expedients exist for each stage of the overall process. The choice of expedients depends on variables such as the plasmid vector system chosen for the cloning and introduction of the recombinant DNA molecule, the plant species to be modified, the particular structural gene, promoter elements, and anaerobic regulatory element used. Persons skilled in the art are able to select and use appropriate alternatives to achieve the end result of functionality.

Homologs of structural genes or of other sequences may be identified by those skilled in the art by the ability of their nucleic acids to cross-hybridize under conditions of appropriate stringency as is well understood in the art (as described in Hames and Higgins (eds.) (1985) *Nucleic Acid Hybridization*, IRL Press, Oxford, UK). It will be understood that there may be minor sequence variations within sequences used or disclosed in this application. These variations may be determined by standard techniques to enable those of ordinary skill in the art to manipulate and bring into utility the functional units of the anaerobic regulatory element, the promoter elements necessary to direct the initiation of transcription, and the structural gene followed by a plant-expressible transcription termination (and perhaps polyadenylation) signal.

The recombinant DNA molecule carrying the desired structural gene under the regulatory control of the anaerobic regulatory element may be introduced into plant tissue by various techniques known to those skilled in the art. The technique used for a given plant species or specific type of plant tissue depends on the known successful techniques. Means for introducing recombinant DNA into plant tissue include, but are not limited to transformation (J. Paszkowski et al. (1984) EMBO J. 3:2717–2722), electroporation (M. Fromm et al (1985) Proc. Natl. Acad. Sci. U.S.A. 82:5824–5828), or microinjection of the DNA (A. Crossway et al. (1986) Mol. Gen. Genet. 202:179–185) or T-DNA-mediated transfer from Agrobacterium to the plant tissue. Representative T-DNA vector systems are described in the following references: G. An et al. (1985) EMBO J. 4:277–284; L. Herrera-Estrella et al. (1983) Nature 303:209–213; L. Herrera-Estrella et al. (1983) EMBO J. 2:987–995; and L. Herrera-Estrella et al. (1985) in *Plant Genetic Engineering*, New York: Cambridge University Press, pp. 63–93. Once introduced into the plant tissue, the expression of the structural gene may be assayed in a transient expression system, or it may be determined after selection for stable integration within the plant genome. Techniques are known for the in vitro culture of plant tissue, and in a number of cases, for regeneration into whole plants. Procedures for transferring the introduced gene from the originally transformed plant into commercially useful cultivars are known to those skilled in the art.

Except as noted hereafter, standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in: Maniatis et al. (1982) Molecular Cloning, Cold Spring Harbor Laboratory, Cold Spring Harbor, N.Y.; Wu (ed.) (1979) Meth. Enzymol. 68; Wu et al., (eds.) (1983) Meth. Enzymol. 100 and 101; Grossman and Moldave (eds.) Meth. Enzymol. 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Method in Molecular Biology;* Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Sellow and Holaender (1979) *Genetic Engineering: Principles and Methods*, Vols. 1–4, Plenum Press, New York. Abbreviations and nomenclature, where employed, are deemed standard in the field and commonly used in professional journals such as those cited herein.

The following non-limiting examples utilize many techniques well known and accessible to those skilled in the arts of molecular biology, the manipulation of recombinant DNA in plant tissue, and the handling and culture of the various forms of plant tissue. Enzymes and molecular biological supplies are obtained from commercial sources and are used according to the vendors' recommendations or other variations known in the art. Reagents, buffers, and cultural conditions are also known to the art.

EXAMPLE 1

This example describes the cloning, transformation, and assay strategy for studying gene regulation and expression mediated by promoter sequence elements and the anaerobic regulatory element from maize Adh1.

1.1 Introduction of recombinant DNA into maize protoplasts

The *Zea mays* c.v. Black Mexican Sweet XII-11 suspension cell line (P. Chourey and D. Zurawski (1981), Theor. Appl. Genet. 59:341–344) was cultured in modified MS medium (C. Green and R. Phillips (1975), Crop Sci. 15:417–421) at 26° C. Protoplasts were isolated according to the protocol of I. Potrykus et al. (1979), Theor. Appl. Genet. 54:209–214, and prepared for electroporation as previously described E. Howard et al., (1987) Planta 170:535–540. For electroporation 100 μg of plasmid DNA was mixed with 1 ml protoplasts (3×10⁶/ml) in HEPES-buffered saline (10 mM HEPES, pH 7.2, 150 mM NaCl) containing 0.2M mannitol (M. Fromm et al. (1985), Proc. Nat. Acad. Sci. U.S.A. 82:5822–5828). Plasmid DNA used for electroporation was twice-purified over CaCl equilibrium gradients to eliminate any possibility of RNA contamination. The mixture of cells and DNA was subjected to a 45° C. heat shock for 5 min, incubated on ice 5 min, and then electroporated, using a capacitor-discharge electroporation apparatus (Fromm et al., 1985), by a single 50 msec pulse at 250 V on ice. Following an additional 10 min incubation on ice, the cells were diluted tenfold with PCM (Chourey and Zurawski, supra).

1.2 Transient expression assays of reporter gene activity

Following electroporation, samples of the protoplasts were divided into two aliquots; one was incubated aerobically (20% oxygen, atmospheric conditions) and the other was incubated anaerobically (5% oxygen/95% nitrogen). In both cases incubation was in the dark at 26° C. for 20 h. The cells in each aliquot were than collected by centrifugation, resuspended in 250 μl 0.25 Tris-Cl, pH 7.5, sonicated, and assayed for chloramphenicol acetyl transferase enzyme activity. Substrate and reaction products were extracted with ethyl acetate and separated by thin layer chromatography as previously described (C. Gorman et al. (1982), Mol. Cell. Biol. 2:1044–1051). The chromatograms were fluorographed and spots quantitated by scintillation counting (Howard et al., 1987). Specifically, thin layer plates were enhanced by fluorography in α-methyl naphthalene containing 0.4% PPO, dried and exposed to X-ray film at −80° C. for 1–4 days.

Each plasmid construction was assayed 2–5 times in separate electroporation experiments. Because of the variation in protoplast preparations and in the efficiency of electroporation, results were normalized to give a value of 1 for the anaerobic expression of pAdhCAT after subtraction of the nonspecific background products as measured using plasmid pAdhCAT- (Howard et al., 1987).

1.3 Cloning and expression of the anaerobically regulated maize Adh1 promoter in maize protoplasts The plasmid pAdhCAT contains the −1094 to +106 region of DNA from the 5′ region of the maize Adh1 gene fused to pCN100. pCN100 was constructed as described in Howard et al., 1987, using a derivative of pNCAT4 (obtained from L. Herrera-Estrella and P. Zambryski) in which the BamHI site linking the CAT coding region to the 3′ nos sequences comprising the polyadenylation signal has been eliminated by cutting with BamHI, filling in with DNA polymerase I and religating. To make pCN100, the BamHI-StuI fragments of the pNCAT4 derivative was ligated to pUC18 which had been restricted with BamHI and HincII. The DNA from the 5′ region of Adh1 (−1094 to +106) was prepared for cloning by Bal31 deletion from the HindIII site in the first intron (E. Dennis et al. (1984) Nucleic Acids Res. 12:3983–4000). BamHI linkers were ligated onto the deletion endpoints after treatment with DNA polymerase I, and then cloned into pUC18 as a BamHI fragment extending from the BamHI site at −1094 to the BamHI linker at the deletion endpoint. The appropriate fragment was chosen after the deleted fragments were characterized by restriction endonuclease mapping and DNA sequence analysis. Thus the Adh1 promoter-containing fragment was fused to pCN100 as a BamHI fragment. pAdhCAT- contains the same maize-derived fragment, but inserted in the reverse orientation with respect to the CAT reporter gene.

pAdhCAT and pAdhCAT- were tested in the transient expression system after electroporation. Cells transformed with pAdhCAT- gave background levels of expression after either aerobic or anaerobic incubation, while cells transformed with pAdhCAT expressed about four-fold more CAT activity after anaerobic than after aerobic incubation. Thus, the 1200 bp upstream of the coding region of Adh1 specifically promote the anaerobic expression of a downstream gene.

1.4 Deletion analysis of the 5′ flanking region of maize Adh1 to localize the anaerobic regulatory element pAdhCAT-140 was constructed by subcloning the PstI fragment of the Adh1 5′ region which extends from −140 to +106 into pUC19 along with the CAT- coding sequences, and the 3′ polyadenylation signal from the *Agrobacterium tumefaciens* T-DNA nopaline synthase gene.

Deletion of 956 bp of 5′ sequence from pAdhCAT to the PstI site at position −140 (pAdhCAT-140) did not alter the anaerobic regulation of the chloramphenicol acetyl transferase reporter gene activity, although the expression level dropped about 25%. Therefore, the approximately 250 bp (−140 to +106) of DNA, 5′ to the coding region of Adh1-S, is sufficient to promote anaerobically regulated expression of the CAT reporter gene in maize protoplasts. This segment of DNA is also capable of anaerobically regulating reporter gene expression in transgenic tobacco when a transcription activating element is incorporated 5′ to the promoter region (J. Ellis et al., U.S. patent application Ser. No. 011,614, filed Feb. 6, 1987).

Progressive 5′ deletions of pAdhCAT-140 were obtained by Bal31 digestion from the SmaI site in the polylinker at the 5′ end of pAdhCAT-140. Following Bal31 digestion and fill-in repair with the Klenow fragment of *E. coli* DNA polymerase I, SalI linkers were attached, the plasmid digested with SalI and HindIII (from the polylinker at the 3′ end of pAdhCAT-140), isolated on low-melting temperature agarose gels, and cloned into pUC19. Generation of 3′ deletions was performed as follows: a pUC19 subcloned fragment of pAdhCAT, containing the Adh1-S promoter only, was digested at a unique SmaI site in the polylinker at the 3′ end of the Adh1 promoter, treated with the Klenow fragment of *E. coli* DNA polymerase I, digested with SalI and BamHI (at position −1094 of the Adh1-S promoter), isolated on low melting temperature agarose gels, and cloned into pUC19. All deletion endpoints were characterized by restriction endonuclease mapping and dideoxy sequencing (E. Chen and P. Seeburg (1985), DNA 4:165–170). The series of Bal31-generated 5′ deletions of pAdhCAT-140 was analyzed to further delineate the sequences necessary for anaerobic control. Deletions to −124 and to −112 dramatically reduced expression (approximately three-fold); however, these deletions retained some degree of anaerobic inducibility. Deletions to −99 and beyond reduced both aerobic and anaerobic levels of reporter gene activity to background. These results indicate that the 5′ boundary of the anaerobic regulatory element is located between −140 and −124. In addition, the difference in expression of the −124 and the −112 deletions compared with the −99 deletion indicated that there are two components to the anaerobic regulatory element.

To determine the 3′ endpoint of the maize Adh1 anaerobic regulatory element, a series of 3′ deletions of the Adh1 promoter, upstream of the TATA box, have been linked to a crippled promoter from the 35S gene of Cauliflower Mosaic Virus (CaMV). p35SCN contains the CaMV 35S promoter, the CAT reporter gene, and the polyadenylation signal from the 3′ region of the nos gene; it was constructed by the isolation of a HincII-HohI fragment of the CaMV 35S gene (bp 7015 to 7450, as numbered by A. Franck et al. (1980), Cell 21:285-294) ligation with BamHI linkers and cloning into the BamHI site at the 5′ end of pCN100 (vide supra, Howard et al., 1987). pΔ 35SCN was constructed by Bal31 deletion from the EcoRV site within the 35S promoter, ligation with SalI linkers, digestion with SalI and HindIII (located in the polylinker at the 3′ end of p35SCN), isolation on low melting temperature agarose gels, and cloning into pUC19. pΔ 35SCN was determined to have an endpoint 45 bp upstream from the cap site of the 35S gene by dideoxy sequencing (E. Chen and R. Seeburg (1985), DNA 4:165-170). Neither p35SCN nor pΔ 35SCN contain any of the transcribed sequences of the 35S gene.

Each of the series of 3′ deletions of the Adh1 promoter fragment were linked to the SalI site at the 5′ end of the crippled 35S promoter in pΔ 35SCN. After electroporation to introduce the plasmids into maize protoplasts, aerobic and anaerobic levels of reporter gene activity were quantified. Fusion of sequences extending from −35 to −1094 or −81 to −1094 of the Adh1-S promoter region conferred anaerobic inducibility on the CAT gene of pΔ 35SCN. Adh1-S sequences deleted upstream of −81 did not allow expression of the reporter gene. These results indicate that sequences located 5′ of position −81 are necessary and sufficient for anaerobically regulated regulation of the downstream genes in maize protoplasts.

1.5 Linker scanning mutagenesis of the Adh1 promoter region

An explanation of linker scanning mutagenesis and its use is given in S. McKnight and R. Kingsbury (1982), Science 217:316-324. The generation of 5′ and 3′ deletions in the Adh1 promoter region was described in Example 1.4. Linker scanning mutations were constructed by joining the SalI linkers of the appropriately matched 3′ deletions to the 5′ deletions. In the case of the pLS-113/-99 the SalI termini were filled in with the Klenow fragment of E. coli DNA polymerase I before ligation so that wild-type spacing between the 5′ and the 3′ components was maintained.

A series of LS mutations in the region between −140 and −81 were constructed to better define the sequences essential for anaerobic regulation. These LS constructions result in clustered point mutations because the wild-type sequence is replaced with that of the linker, but do not greatly change the spacing between non-mutated sequences. Plasmids are named according to the extent of wild-type sequence present; for example, pLS−133/−124 contains the wild-type Adh1 sequence from −140 to −133, the SalI linker, and wild-type Adh1 sequence from −124 to the 3′ end of the Adh1 promoter fragment, i.e. the sequence −133/−124 is replaced with linker sequence.

One mutant, pLS−133/−124, exhibited reduced expression to the level observed under aerobic conditions. This was similar to the results observed with the 5′ deletions to −124 or to −112 except that pLS−133/−124 did not appear to be inducible. Another mutant pLS−113/−99 did not express reporter gene activity above background levels regardless of oxygen availability. These results indicate that sequences within the −133/−124 region and the −113/−99 regions are required for anaerobic expression of Adh1. Other LS mutants having deletions between these two regions, pLS−125/−117 and pLS−116/−107, did not greatly affect anaerobic CAT expression relative to pAdhCAT. In addition, LS mutants pLS−99/−92, pLS−89/−81, and pLS−80/−72, had no apparent effect on the anaerobic expression of reporter gene activity.

These results indicate that the 5′ boundary of the anaerobic regulatory element is between −140 and −133, while the 3′ boundary is between −99 and −113. The anaerobic regulatory element contains two component regions, associated with the mutants pLS−133/−124 (Region I) and by pLS−113/−99 (Region II), with DNA sequence between these two regions subject to mutation without any discernable effect on anaerobically regulated gene expression. Based on these results the maize Adh1 anaerobic regulatory element was identified to be composed of the two sequence elements displayed in FIG. 1. Both sequence elements were found to be required for efficient anaerobic induction of chimaeric genes.

EXAMPLE 2

This example describes the cloning and sequencing of the maize aldolase gene and the analysis of the aldolase 5′ upstream regions.

2.1 Cloning and Sequencing of the Maize Aldolase Gene

Anaerobic specific cDNA clones were synthesized from RNA extracted from anaerobically induced maize seedlings (Gerlach et al. (1982) Proc. Natl. Acad. Sci U.S.A. 82:5822-5828) and classified by cross-hybridization and hybrid-release translation products. One clone, pZML54, contained a 500 bp insert which hybrid selected two proteins of approximately 37,000 and 35,000 kd MW and had a nucleotide sequence coding a sequence of amino acids homologous to animal aldolase (Rottman et al. (1984) Proc. Natl. Acad. Sci. U.S.A. 81:2738-2742; Tolan et al. (1984) J. Biol. Chem. 259:1127-1131). Kelley and Tolan (1986) Plant Physiol. 82:1076-1080 have isolated a full-length cDNA coding for aldolase from anaerobically induced maize seedlings which they sequenced and identified as the cytoplasmic form of aldolase.

The cDNA insert from pZML54 was excised from the plasmid, radioactively labelled by nick translation and used as a probe for plaque hybridization of a partial Sau3A digested maize genomic library in lambda EMBL4 (Frischauf et al. (1983)). Two positively hybridizing genomic clones were isolated and shown by restriction enzyme mapping to contain identical maize DNA internal sequences. One of these genomic clones, lambda 54, was selected for further analysis and subcloned into pUC8 to give the plasmid pAN54.

DNA sequences were determined using the dideoxynucleotide chain termination method (Sanger et al. (1977) Proc. Natl. Acad. Sci. U.S.A. 74:5463–5467) after subcloning of restriction enzyme fragments of cDNA and genomic clones into the phage vectors mp10 and 11 or mp18 and 19 (Messing and Vieira (1982) Gene 19269–276). In order to sequence both strands completely, oligonucleotides chosen to fill gaps in the sequence were synthesized on a commercial DNA synthesizer and used as primers in the dideoxy sequencing reactions.

Sequencing of the pZML54 insert and comparison of the sequence to the EMBL database showed approximately 50% amino acid sequence homology to rabbit and rat aldolase consistent with the pZML54 insert corresponding to the aldolase (1,6 diphosphate aldolase) gene. It appears that the pZML54 insert is a partial cDNA clone for maize aldolase.

The sequence of the genomic clone in the gene coding region is very similar to that of the full-length cDNA for cytoplasmic maize aldolase (Kelley and Tolan, 1986). Five single base differences in the coding region of the gene were found, however these differences result in only a single amino acid change at position 263. Further comparison of the genomic sequence with the sequences of both the full-length and pZML54 cDNA clones showed the presence of single intron in the genomic coding region beginning 9 codons after (5') the ATG initiation codon and extending 800 bp. In the genomic clone there is one extra base in the 5' untranslated leader region immediately upstream of the ATG compare to the cDNA sequence.

The start of transcription of the aldolase gene was mapped using S$_1$ nuclease protection of the 5' region of the gene by anaerobically induced RNA as previously described Dennis et al. (1984) Nucl. Acids Res. 12:3903–4000. The length of the 5' untranslated region was 65 bp. There is a TAATA box 31 bp upstream from the start of transcription.

2.2 Construction of an anaerobic expression of the chimaeric plasmid pAldCAT and pAldCAT- The 5' region of the aldolase gene extending from a HindIII site at −700 to a ClaI site at +80 bp (i.e. 3 bp upstream of the ATG initiation codon) was excised from the genomic clone lambda 54. The resulting fragment was then ligated into HindIII/AccI-cut pUC8. The chimaeric plasmid was transformed into *E. coli* strain DH1 and DNA was prepared. A BamHI fragment was then excised from the plasmid and ligated into phosphatased BamHI-cut pCN100 (Howard et al., 1987). Two plasmids resulted, pAldCAT and pAldCAT− which contain the aldolase gene upstream region fragment insert in both orientations with pAldCAT- containing the fragment in inverse orientation.

Both pAldCAT and pAldCAT− were tested in the transient expression system after electroporation for CAT activity assayed after 24 hr. Cells transformed with pAldCAT- gave background levels of cat gene expression after either aerobic or anaerobic incubation, while cells transformed with pAldCAT expressed 7 times the background level after anaerobic than after aerobic incubation. These results indicate that the approximate 800 bp region immediately upstream of the ATG initiation codon contains information necessary for the expression of the aldolase gene.

We claim:

1. A recombinant DNA molecule comprising:
   (a) an anaerobic regulatory element;
   (b) a plant-expressible promoter located 3' to said anaerobic regulatory element, and
   (c) a plant-expressible structural gene located 3' to said plant-expressible promoter such that said structural gene is placed under the regulatory control of said promoter and said anaerobic regulatory element wherein said structural gene is not in nature under the regulatory control of said anaerobic regulatory element.

2. The DNA molecule of claim 1 wherein said anaerobic regulatory element comprises the consensus sequence:

5'-BBTGGTTTBB-3' where B is C, T or G.

3. The DNA molecule of claim 2 wherein said anaerobic regulatory element comprises the nucleotide sequence 5'-GCTGGTTTCT-3'.

4. The DNA molecule of claim 2 which comprises the nucleotide sequence of the DNA fragment extending from about nucleotide −805 to +72 in the 5' region upstream of the maize aldolase gene.

5. The DNA molecule of claim 1 wherein said anaerobic regulatory element comprises the region II sequence:

5'-CGTGGTTTGCTTGCC-3'.

6. The DNA molecule of claim 5 which comprises the nucleotide sequence of the DNA fragment extending from about −124 to about +106 in the 5' region upstream of the maize Adh1 gene.

7. The DNA molecule of claim 5 which comprises the nucleotide sequence of the DNA fragment extending from about −112 to about +106 in the 5' region upstream of the maize Adh1 gene.

8. The DNA molecule of claim 1 wherein said anaerobic regulatory element comprises the region I sequence:

5'-CTGCAGCCCCGGTTTCG-3'.

9. The DNA molecule of claim 1 wherein said anaerobic regulatory element comprises both the region I and the region II sequences, wherein the region I sequence is:

5'-CTGGAGCCCCGGTTTCG-3' and the region II sequence is:

5'-CGTGGTTTGCTTGCC-3'.

10. The DNA molecule of claim 9 which comprises the nucleotide sequence of the DNA fragment extending from about −140 to about −99 in the 5' region upstream of the maize Adh1 gene.

11. The DNA molecule of claim 9 which comprises the nucleotide sequence of the DNA fragment extending from about −140 to about −81 in the 5' region upstream of the maize Adh1 gene.

12. The DNA molecule of claim 5 comprises the DNA fragment extending from about −1094 to about +106 of the maize Adh1 gene.

13. The DNA molecule of claim 1, wherein said anaerobic regulatory element comprises the region II sequence:

5'-CGAGCCTTTCTTCCC-3'.

14. The DNA molecule of claim 1, wherein said anaerobic regulatory element comprises the region I sequence:

5'-CTGCCTCCCTGGTTTCT-3'.

15. The DNA molecule of claim 1, wherein said anaerobic regulatory element comprises both the region I and region II sequences, wherein the region I sequence is:

5'-CTGCCTCCCTGGTTTCT-3' and the region II sequence is:

5'-CGAGCCTTTCTTCCC-3'.

16. The recombinant DNA molecule of claim 2 wherein said anaerobic regulatory element is of an anaerobically induced gene of a monocot.

17. The recombinant DNA molecule of claim 2 wherein said anaerobic regulatory element is of an anaerobically induced gene of maize.

18. The recombinant DNA molecule of claim 1 wherein said plant expressible structural gene encodes an enzyme, the activity of which can be quantified.

19. The recombinant DNA molecule of claim 18 wherein said enzyme is chloramphenicol acetyl transferase.

20. The recombinant DNA molecule of claim 1 wherein said plant-expressible promoter is derived from a plant alcohol dehydrogenase gene.

21. The recombinant DNA molecule of claim 1 wherein said plant-expressible promoter is derived from Cauliflower Mosaic Virus.

* * * * *

UNITED STATES PATENT AND TRADEMARK OFFICE
CERTIFICATE OF CORRECTION

PATENT NO. : 5,001,060

DATED : March 19, 1991

INVENTOR(S) : James W. Peacock, John C. Walker, Elizabeth Dennis, Elizabeth A. Howard It is certified that error appears in the above-identified patent and that said Letters Patent is hereby corrected as shown below: On the title page:

In the References Cited section, second column, line 11, rewrite "Nol." as --Mol.--. Column 2, lines 53-55, rewrite "for accurate -80 and -100, there can be a promoter element with transcription initiation. Further upstream, often between homology" as --for accurate transcription initiation. Further upstream, often between -80 and -100, there can be a promoter element with homology--. Column 3, line 19, insert --Odell et al. (1985) Nature 313:810-812, have shown that-- between "J." and "sequences".

Signed and Sealed this

Thirteenth Day of October, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 5,001,060

DATED : March 19, 1991

INVENTOR(S) : James W. Peacock, et al.

It is certified that error appears in the above-identified patent and that said Letters Patent is hereby corrected as shown below:

Column 5, line 8, rewrite "In the" as --The--. Column 12, line 31, rewrite "Wu et al.," as --Wu et al.--. Column 12, line 39, rewrite "Vol." as --Vols.--. Column 13, line 5, rewrite "described E. Howard" as --described. E. Howard--. Column 13, line 29, rewrite "than" as --then--. Column 13, line 48, rewrite "pAdhCAT-" as pAdhCAT⁻--. Column 14, line 9, rewrite "CAT-" as --CAT⁻--. Column 14, line 13, rewrite "pAdhCAT⁻--. Column 14, line 15, rewrite "pAdhCAT-" as --pAdhCAT⁻--. Column 14, line 25, rewrite "pAdhCAT-140" as --pAdhCAT⁻140--. Column 14, line 27, rewrite "CAT-" as --CAT⁻--. Column 14, line 32, rewrite "(pAdhCAT-140)" as --(pAdhCAT⁻140)--. Column 14, line 45, rewrite "pAdhCAT-140" as --pAdhCAT⁻140--. Column 14, line 47, rewrite "pAdhCAT-140" as --pAdhCAT⁻140--. Column 14, line 51, rewrite "pAdhCAT-140" as --pAdhCAT⁻140--. Column 14, line 65, rewrite "pAdhCAT-140" as --pAdhCAT⁻140--. Column 15, line 18, rewrite "HohI" as --HphI--. Column 17, line 9, rewrite "19269-276" as --19:269-276--. Column 17, line 18, rewrite "1,6 diphosphate aldolase)" as --(1,6-diphosphate aldolase)--. Column 17, line 38, rewrite "described Dennis et al." as --described. Dennis et al.--.

UNITED STATES PATENT AND TRADEMARK OFFICE
CERTIFICATE OF CORRECTION

PATENT NO. : 5,001,060

DATED : March 19, 1991

INVENTOR(S) : James W. Peacock, John C. Walker, Elizabeth Dennis & Elizabeth A. Howard It is certified that error appears in the above-identified patent and that said Letters Patent is hereby corrected as shown below:

Column 17, line 43, rewrite "Construction of an" as --Construction and--.
Column 17, line 44, rewrite "plasmid" as --plasmids--. Column 17, line 44, rewrite "pAldCAT-" as --pAldCAT$^-$--. Column 17, line 57, rewrite "CAT-" as --CAT$^-$--. Column 17, line 61, rewrite "pAldCAT-" as --pAldCAT$^-$--.

Signed and Sealed this

Twelfth Day of January, 1993

*Attest:*

DOUGLAS B. COMER

*Attesting Officer*      *Acting Commissioner of Patents and Trademarks*